US007326180B2

(12) United States Patent
Tanabe et al.

(10) Patent No.: US 7,326,180 B2
(45) Date of Patent: Feb. 5, 2008

(54) PULSE WAVE MONITORING DEVICE

(75) Inventors: Kazuhisa Tanabe, Kyoto (JP); Tomoki Kitawaki, Okayama (JP); Kazunobu Itonaga, Kyoto (JP); Hironori Sato, Moriyama (JP); Masao Hashimoto, Kyoto (JP); Yoshinori Miyawaki, Otsu (JP)

(73) Assignee: Omron Healthcare Co., Ltd., Kyoto (JP)

( * ) Notice: Subject to any disclaimer, the term of this patent is extended or adjusted under 35 U.S.C. 154(b) by 329 days.

(21) Appl. No.: 10/727,043

(22) Filed: Dec. 4, 2003

(65) Prior Publication Data
US 2004/0167414 A1 Aug. 26, 2004

(30) Foreign Application Priority Data
Dec. 5, 2002 (JP) ............................. 2002-353896
Oct. 1, 2003 (JP) ............................. 2003-343321

(51) Int. Cl.
*A61B 5/02* (2006.01)
(52) U.S. Cl. ...................... 600/500; 600/300; 600/485; 600/490
(58) Field of Classification Search ................ 600/300, 600/485, 490, 500
See application file for complete search history.

(56) References Cited
U.S. PATENT DOCUMENTS

| 5,265,011 | A | | 11/1993 | O'Rourke | |
|---|---|---|---|---|---|
| 5,309,916 | A | * | 5/1994 | Hatschek | 600/485 |
| 6,616,613 | B1 | * | 9/2003 | Goodman | 600/504 |
| 6,702,754 | B2 | * | 3/2004 | Ogura et al. | 600/500 |
| 6,884,221 | B2 | * | 4/2005 | Narimatsu et al. | 600/485 |
| 2001/0056228 | A1 | * | 12/2001 | Utsugi et al. | 600/300 |
| 2002/0091328 | A1 | | 7/2002 | Ogura | |
| 2003/0004422 | A1 | * | 1/2003 | Narimatsu | 600/500 |
| 2003/0013988 | A1 | * | 1/2003 | Kodama et al. | 600/551 |
| 2003/0083580 | A1 | * | 5/2003 | Tampo et al. | 600/490 |
| 2003/0139675 | A1 | * | 7/2003 | Ogura et al. | 600/492 |
| 2004/0077960 | A1 | * | 4/2004 | Tanaka et al. | 600/504 |

FOREIGN PATENT DOCUMENTS

JP 11-332837 5/1998

(Continued)

OTHER PUBLICATIONS

European Search Report dated Apr. 6, 2004.

(Continued)

*Primary Examiner*—Charles A. Marmor, II
*Assistant Examiner*—Karen E Toth
(74) *Attorney, Agent, or Firm*—Morrison & Foerster LLP

(57) ABSTRACT

A sensor is pressurized adjustably against a patient's wrist and detects a pressurized pulse wave of a radial artery in a noninvasive manner so as to measure blood pressure on an arm band wound around the patient's predetermined portion. A CPU calculates indices reflecting a reflecting phenomenon of a pulse wave as organism information different from the blood pressure based on the detected pulse waveform, and relates the measured blood pressure value with calculated indices so as to display them on an indicator. A doctor checks displayed contents so as to clearly understand a state of a circulatory system represented by a correlation between the patient's blood pressure and the indices so as to be capable of obtaining information which supports a diagnosis and prescription quickly.

12 Claims, 14 Drawing Sheets

FOREIGN PATENT DOCUMENTS

| | | |
|---|---|---|
| JP | 2000-217796 | 2/1999 |
| JP | 2000-316821 | 5/1999 |
| JP | 2000-139859 | 5/2000 |
| JP | 2003-210422 | 7/2003 |
| WO | WO 02/05726 A2 | 7/2001 |

OTHER PUBLICATIONS

BP McGrath et al., "Impact of Physical and Physiological Factors on Arterial Function", Clinical and Experimental Pharmacology and Physiology (2001) 28, pp. 1104-1107.

J. Cameron et al., "Use of Radial Artery Applanation Tonometry and a Generalized Transfer Function To Determine Aortic Pressure Augmentation in Subjects with Treated Hypertension", JACC vol. 32, No. 5, Nov. 1, 1998, pp. 1214-1220.

I. Wilkinson et al., "The Influence of Heart Rate on Augmentation Index and Central Arterial Pressure in Humans", Journal of Physiology (2000), 525.1, pp. 263-270.

W. Nichols et al., "Arterial Elastance and Wave Reflection Augmentation of Systolic Blood Pressure: Deleterious Effects and Implications for Therapy", J. Cardiovasc Pharmacol Therapeut 6(1) (2001), pp. 5-21.

* cited by examiner

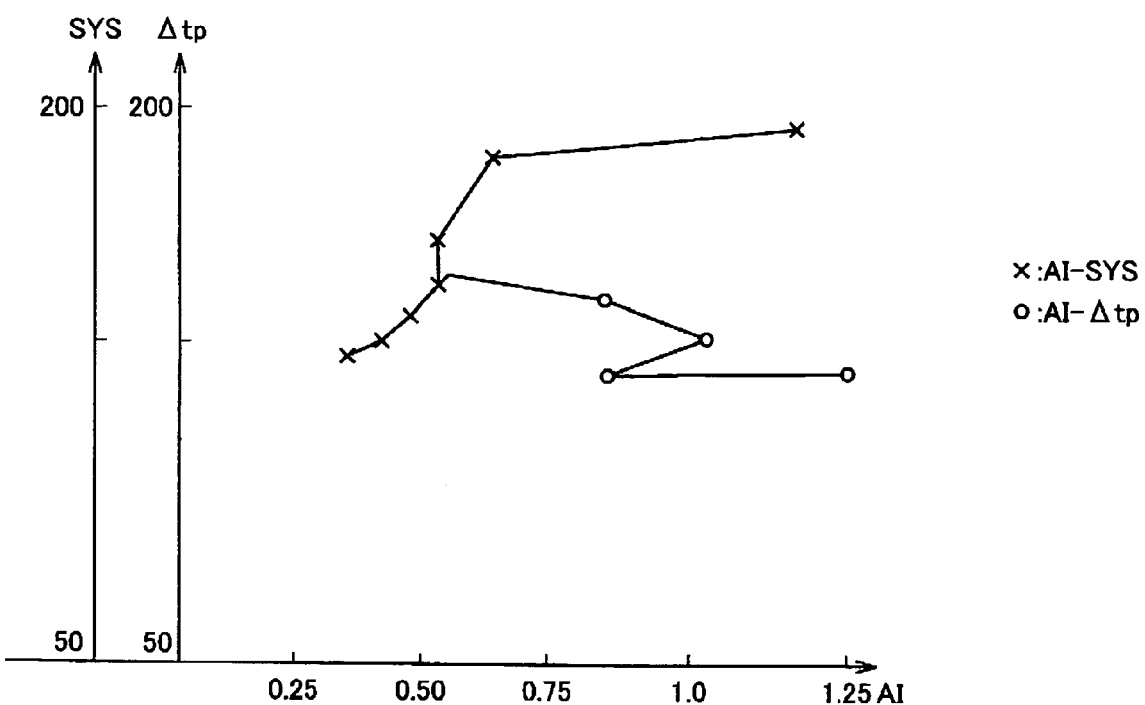

PULSE WAVE MONITORING DEVICE

BACKGROUND OF THE INVENTION

1. Field of the Invention

The present invention relates to a pulse wave monitoring device for monitoring a pulse wave of an organism and, more particularly, to a pulse wave monitoring device for supporting a diagnosis.

2. Description of the Related Art

In close examinations for diagnosing cardio vascular diseases such as hypertension, anbulatory blood pressure monitoring, echocardiography using an ultrasonic diagnostic unit, eyegrounds test, electrocardiography, exercise tolerance test, and the like are conducted. The blood pressure measurement is, however, conducted the most widely as the examinations including the close examinations to general diagnosis. This is because the blood pressure measurement has excellent characteristics such that it can be conducted simply in a noninvasive manner and a measuring device is more inexpensive than devices for another examinations.

Since information obtained form the blood pressure measurement, however, includes only information about whether a blood pressure is at a notable level, the blood pressure measurement judges whether an examinee is a hypertensive patient. A doctor should overall determine, however, how to cure a disease based on information obtained from another examined results and inquiry. The information obtained from the inquiry occasionally includes patient's subjective information, and this occasionally causes misdiagnosis.

In order to conduct more excellent diagnoses of cardio vascular diseases, it is desired, therefore, to provide objective information which supports diagnosis of hypertension and determination of a curing way to doctors without deteriorating the excellent characteristics of the blood pressure measurement.

In order to respond such a request, different two physiologic indices (an adjusted pulse wave velocity and blood pressure index of ankle/upper arm) are expressed by a two-dimensional graph, so that a state transition of a patient can be easily known (see, for example, Specification and Drawings of Japanese Patent Application Laid-Open No. 2000-316821).

Further in order to easily understand the patient's state, a device, that expresses the different two physiologic indices (diastolis pressure and classified results of waveforms of acceleration plethysmogram obtained by a pulse wave pattern classifying unit) using a two-dimensional graph, is also suggested (for example, Specification and Drawings of Japanese Patent Application Laid-Open No. 2000-217796).

Further, a device, that expresses the two kinds of the physiologic indices using the two-dimensional graph and displays a circulating state of a patient, is also suggested (for example, Specification and Drawings of Japanese Patent Application Laid-Open No. 11-332837 (1999)). As a combination of the two physiologic indices includes: a combination 1 of systole time and pulse rate variability; a combination 2 of systole time and blood pressure; a combination 3 of classification of the waveform of the acceleration plethysmogram by the pulse wave pattern classifying unit and blood pressure; a combination 4 of pule wave propagating time; and a combination 5 of systole time and arteriosclerosis.

In the device in Japanese Patent Application Laid-Open No. 2000-316821, however, pulse waves and blood pressure at two points separated from each other should be measured in the measurement of an adjusted pulse wave velocity and an blood pressure index of an ankle/an upper arm. For this reason, the measurement is complicated and cannot be conducted simply.

In the device of Japanese Patent Application Laid-Open No. 2000-217796, since a correlation between the classified result of the waveform of the acceleration plethysmogram by the pulse wave pattern classifying unit and the other physiologic indices is not clear, the classified result is not generally used for clinical diagnoses. Further, as explained in embodiments, the waveform of the acceleration plethysmogram is classified mostly on a tip of finger by the pulse wave pattern classifying unit. Since the tip of finger is, however, easily influenced by environmental temperature, mental stress and the like, it is difficult to collect plethysmogram with stability and reproducibility. For this reason, the result of classifying the acceleration plethysmogram by the pulse wave pattern classifying unit is unstable and has insufficient reproducibility, and the use of the classified result possibly causes misdiagnosis.

In the embodiments, a tip of finger pulse wave is monitored by photo electric plethysmogram pulse wave. The photo electric plethysmogram pulse wave shows a waveform which is deformed by nonlinearity between intravascular pressure and vascular capacity. An compositive element is mixed in the result of classifying the waveform of the acceleration plethysmogram in the photo electric plethysmogram by the pulse wave pattern classifying unit, and physiologic meaning of this result become unclear.

The combinations 3 and 5 in the device of the Japanese Patent Application Laid-Open No. 11-332837 (1999) have the same problem as that in the device of the Japanese Patent Application Laid-Open No. 2000-217796, and the combination 4 has the same problem as that in Japanese Patent Application Laid-Open No. 2000-316821. Since the combinations 1, 2 and 4 do not use characteristic parameters of the pulse wave, a diagnosis cannot be supported by presenting the characteristic parameters obtained based on the pulse wave.

SUMMARY OF THE INVENTION

It is an object of the present invention to provide a pulse wave monitoring device for supporting a diagnosis by presenting characteristic parameters of a pulse wave as information of a circulatory system other than blood pressure to a doctor without deteriorating simplicity of measurement.

A pulse wave monitoring device according to an aspect of the present invention includes: a pulse wave detection device configured to detect a pulse wave of a subject; a computation unit that identifies a plurality of characteristic points of the pulse wave detected by the pulse wave detection device, calculates a plurality of characteristic parameters corresponding to the identified characteristic points and calculates an index indicative of a pulse wave reflection by performing a computation on the characteristic parameters; a blood pressure measuring device configured to measure a blood pressure of the subject; and a display unit that shows the calculated index and the measured blood pressure.

The pulse wave detection device detects a pulse wave of a radial artery to be measurable in a noninvasive manner. The computation unit computes indices of a pulse wave reflection as organism information different from the blood pressure measured by the blood pressure measuring device. The blood pressure values and the index are displayed in a related manner. For this reason, a doctor checks displayed contents so as to be capable of clearly understanding a state of a circulatory system represented by a correlation between the blood pressure and the index of the subject and obtaining information which supports a diagnosis and prescription quickly. Besides the display on a screen, such a display includes outputs obtained by printing via a printer and data transmission to another system.

Preferably, a first characteristic point of the characteristic points corresponds to a peak of a traveling wave component of the detected pulse wave and a second characteristic point of the characteristic points corresponds to a peak of a reflection wave component of the detected pulse wave, the reflection wave component being generated as a result of a reflection of the traveling wave component, and the index is a ratio of amplitudes of the pulse wave at the first and second characteristic points. The index can be, therefore, calculated easily.

Preferably, a first characteristic point of the characteristic points corresponds to a traveling wave component of the detected pulse wave and a second characteristic point of the characteristic points corresponds to a reflection wave component of the detected pulse wave, the reflection wave component being generated as a result of a reflection of the traveling wave component, and the index is a time difference between the first and the second characteristic points. The index can be, therefore, calculated easily.

Preferably, the computation unit adjusts the calculated index based on an adjustment factor of the subject. After the index is adjusted and calculated for each subject, therefore, the index and the blood pressure are related with each other so as to be displayed. For this reason, a state transition can be displayed more accurately than that of the circulatory system of each subject.

Preferably, the index comprises an augmentation index (AI). The AI is, therefore, calculated as reflection information about the pulse wave which is organism information different from the blood pressure, and the AI and the blood pressure can be related with each other so as to be displayed. For this reason, this index can support a doctor in understanding a state of the circulatory system of the subject and in diagnosis and prescription.

Preferably, the computation unit adjusts the calculated AI based on a pulse of the subject. A change in the reflection information about the pulse wave according to a pulse rate (the pulse is quick or slow) can be absorbed by the adjustment.

Preferably, the index comprises $\Delta Tp$. $\Delta Tp$ is defined by a time difference between a starting point (rise point) of a cardiac ejected wave and a starting point of the reflection wave. The starting point means a position where a pulse wave acceleration becomes maximal (as an algorithm process, a position of a zero-cross point of a pulse waveform according to cubic differentiation). $\Delta Tp$ is, therefore, calculated as the reflection information about the pulse wave which is the organism information different from the blood pressure, and $\Delta Tp$ and the blood pressure are related with each other so as to be displayed. For this reason, this index can support a doctor in understanding a state of the circulatory system of the subject and in diagnosis and prescription.

Preferably, the computation unit adjusts the calculated $\Delta Tp$ based on a height of the subject. A change in the reflection information about the pulse wave according to the height can be absorbed by the adjustment.

The pulse wave monitoring device preferably further includes a memory device that stores a plurality of the calculated indices and a plurality of the measured blood pressures in a chronological order.

The indices calculated by different timing pulse wave measurement on the subject and the blood pressures measured by the blood pressure measuring unit can be stored in the chronological order.

The display unit preferably shows the calculated indices and the measured blood pressures in the chronological order. The indices and the blood pressures calculated and measured in the past are related with each other so as to be displayed in the chronological order. For this reason, the doctor checks the displayed contents so as to understand the state transition of the circulatory system represented by a correlation between the blood pressures and the indices of the subject according to passage of time. As a result, the doctor can check good or bad effect of a cure including an effect of prescribed medicine quickly.

A pulse wave monitoring device according to another aspect of the invention includes: a pulse wave detection device configured to detect a pulse wave of a subject; a computation unit that calculates a plurality of different indices based on a waveform of the detected pulse wave, each of the different indices being indicative of a pulse wave reflection; and a display unit that shows a correlation between at least two of the different indices. The display includes outputs by printing via a printer and data transmission to another system in addition to the display on a screen.

The pulse wave detection device detects a pressured pulse wave of a radial artery to be measurable in a noninvasive manner. The computation unit computes a plurality of indices of a pulse wave reflection as organism information different from the blood pressure. The calculated indices are displayed in a related manner. For this reason, a doctor checks displayed contents so as to be capable of clearly understanding a state of a circulatory system represented by a correlation between the indices of the subject and obtaining information which supports a diagnosis and prescription quickly.

Preferably, the display unit shows a prescription determined based on the correlation.

When the indices are displayed, therefore, information about medicine to be prescribed is also displayed according to the levels of the related indices. For this reason, a doctor understands and diagnoses the state of the circulatory system of the subject, and simultaneously can obtain the information about a prescription.

Preferably, the pulse wave monitoring device further includes: a blood pressure measuring device configured to measure a blood pressure of the subject, wherein the display unit configured to show a correlation between the measured blood pressure and at least one of the difference indices.

The pulse wave detection device detects a pressured pulse wave of a radial artery to be measurable in a noninvasive manner. The computation unit calculates indices of a pulse wave reflection as organism information different from the blood pressure measured by the blood pressure measuring device. The blood pressure values and the index are displayed in a related manner. For this reason, a doctor checks displayed contents so as to be capable of clearly understanding a state of a circulatory system represented by a correlation between the blood pressure and the index of the subject and obtaining information which supports a diagnosis and prescription quickly.

Preferably, the pulse wave monitoring device further includes a memory device that stores a plurality of the calculated indices for each of the different indices in a chronological order.

The indices calculated by different timing pulse wave measurement on the subject can be stored according to a plurality of groups in the chronological order.

Preferably, the groups further includes blood pressures measured by the blood pressure measuring device. The indices calculated by different timing pulse wave measurement on the subject and the blood pressures measured by the blood pressure measuring device can be, therefore, stored in the chronological order according to the groups.

Preferably, the display unit shows the calculated indices stored in the memory device for at least two of the different indices in the chronological order. The indices calculated in the past are related with each other so as to be displayed in the chronological order. For this reason, the doctor checks the displayed contents so as to understand the state transition of the circulatory system represented by a correlation between the indices of the subject according to passage of time. As a result, the doctor can check good or bad effect of a cure including an effect of prescribed medicine quickly.

Preferably, the display unit shows the calculated indices stored in the memory device for at least one of the different indices and the measured blood pressures stored in the memory device in the chronological order.

At least one of the calculated indices and the detected blood pressures are, therefore, related so as to be displayed in the chronological order. For this reason, a doctor checks the displayed contents so as to be capable of understanding a state transition of the circulatory system represented by a correlation between the blood pressure and the indices of the subject according to passage of time. As a result, the doctor can check good or bad effect of a cure including an effect of prescribed medicine quickly.

Preferably, the computation unit adjusts at least one of the different indices based on an adjustment factor of the subject. After the index is adjusted and calculated for each subject, therefore, the index and the blood pressure are related with each other so as to be displayed. For this reason, a state transition can be displayed more accurately than that of the circulatory system of each subject.

Preferably, one of the indices comprises an augmentation index. The AI is, therefore, calculated as reflection information about the pulse wave which is organism information different from the blood pressure, and the AI and the blood pressure or another index can be related with each other so as to be displayed. For this reason, this index can support a doctor in understanding a state of the circulatory system of the subject and in diagnosis and prescription.

Preferably, the computation unit adjusts the calculated augmentation index based on a pulse of the subject. A change in the reflection information about the pulse wave according to a pulse rate (the pulse is quick or slow) can be, therefore, absorbed by the adjustment.

Preferably, one of the indices comprises $\Delta Tp$. $\Delta Tp$ is defined by a time difference between a starting point (rise point) of a cardiac ejected wave and a starting point of the reflection wave. The starting point means a position where a pulse wave acceleration becomes maximal (as an algorithm process, a position of a zero-cross point of a pulse waveform according to cubic differentiation). $\Delta Tp$ is, therefore, calculated as the reflection information about the pulse wave which is the organism information different from the blood pressure, and $\Delta Tp$ and the blood pressure or another index are related with each other so as to be displayed. For this reason, this index can support a doctor in understanding a state of the circulatory system of the subject and in diagnosis and prescription.

Preferably, the computation unit adjusts the calculated $\Delta Tp$ based on a height of the subject. A change in the reflection information about the pulse wave according to the height can be, therefore, absorbed by the adjustment.

The display unit shows a prescription determined based on a correlation between one of the indices and the blood pressure.

When the index and the blood pressure are, therefore, related so as to be displayed, the information about medicine to be prescribed according to a level of the related index and blood pressure is also displayed. For this reason, a doctor understands and diagnoses the state of the circulatory system of the subject, and simultaneously can obtain the information about a prescription.

The correlation is represented by an arbitrary point (coordinate (X, Y)) on a plane when a value of one index (or blood pressure) is plotted on one straight line and a value of another index (or blood pressure) is plotted on another straight line on a plane determined by crossing two straight lines (X axis, Y axis).

Further, the correlation is represented by an arbitrary point (coordinate (X, Y, Z)) in a space when a value of one index (blood pressure) is plotted on one straight line, a value of another index (or blood pressure) is plotted on another straight line and a value of still another index (or blood pressure) is plotted on a still another straight line in a cubic space determined by crossing three straight lines (X axis, Y axis, Z axis).

BRIEF DESCRIPTION OF THE DRAWINGS

FIG. 17 is a diagram illustrating another example of display in which AI, ΔTp and the maximal blood pressure SYS are related with each other.

DETAILED DESCRIPTION OF THE PREFERRED EMBODIMENTS

The embodiments of the present invention are explained in detail below with reference to the drawings.

Figure 1:
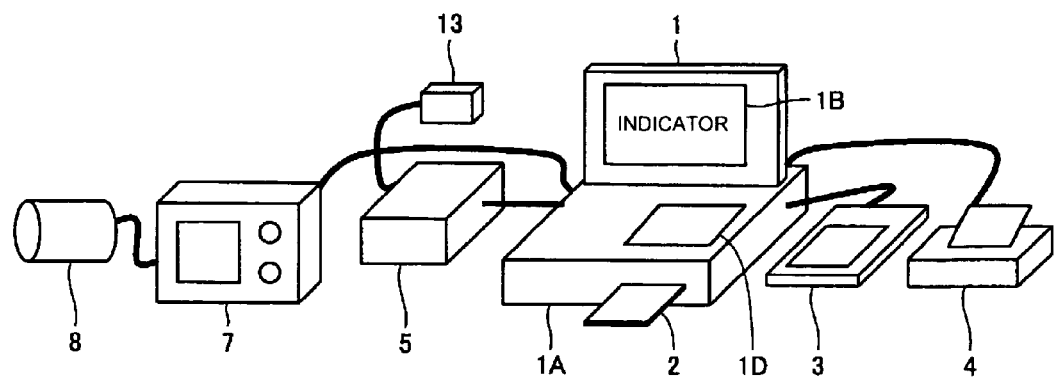
FIG. 1 is a diagram illustrating one example of an appearance of a pulse wave monitoring device for supporting a diagnosis according to an embodiment.
Figure 2:
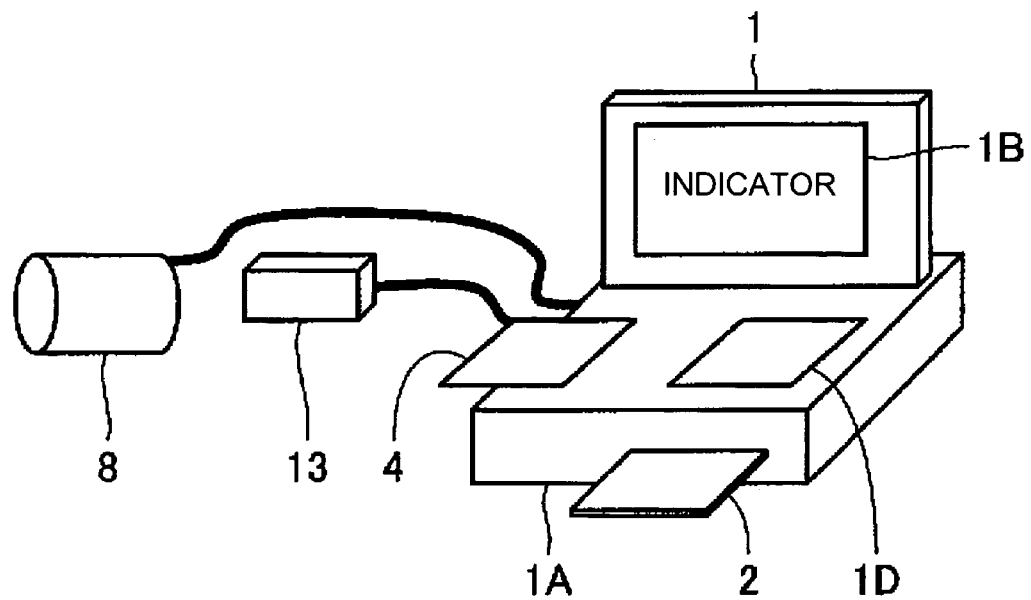
FIG. 2 is a diagram illustrating another example of the appearance of the pulse wave monitoring device for supporting a diagnosis according to the embodiment.
Figure 3:
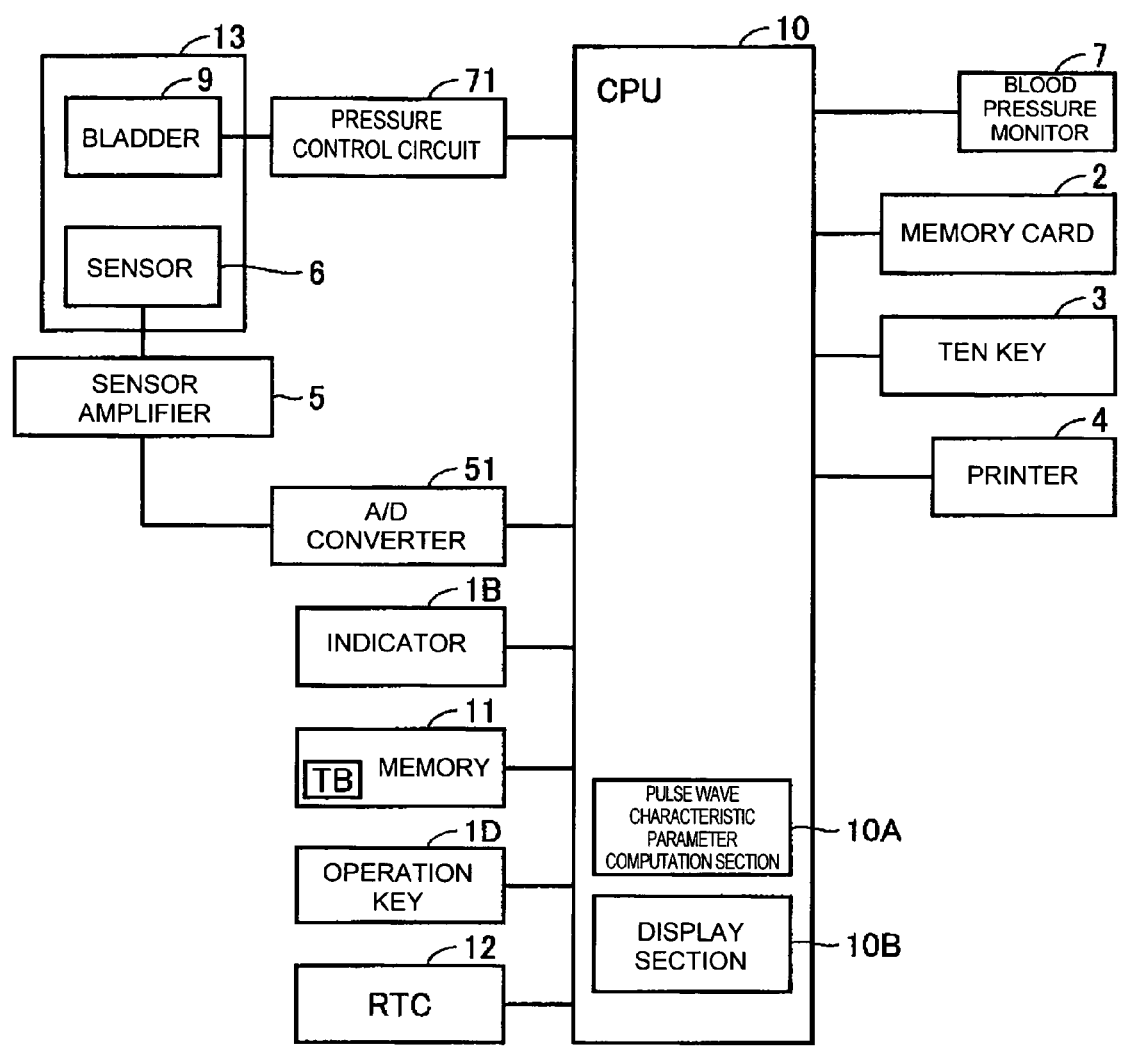
FIG. 3 is a system constitutional diagram of the pulse wave monitoring device for supporting a diagnosis according to the embodiment.

FIGS. 1 and 2 illustrate appearances of a pulse wave monitoring device for supporting a diagnosis according to an embodiment. FIG. 1 shows the appearance in the case where the device is separated into a plurality of units, and FIG. 2 shows the appearance in the case where the device includes the units. FIG. 3 illustrates a system constitution of the pulse wave monitoring device.

In FIGS. 1 to 3, the pulse wave monitoring device for supporting a diagnosis includes a PC (personal computer) 1, a memory card 2, a ten key 3, a printer 4, a sensor amplifier 5, a blood pressure monitor 7, a sensor unit 13, and an arm band 8. The PC 1 has a main body 1A, an indicator 1B and an operation key 1D for displaying various pieces of information on an external portion in an integral manner, and contains a CPU (central processing unit) 10, a memory 11 and a RTC (real time clock) 12. The memory card 2 is attached to the PC 1 detachably. The ten key 3, the printer 4, the sensor amplifier 5 and the blood pressure monitor 7 are detachably connected to the PC 1 via cables. The sensor unit 13 is connected with the sensor amplifier 5. The band arm 8 is connected with the blood pressure monitor 7 and has a bladder. The sensor unit 13 contains a sensor 6 and a bladder 9 which pressurizes the sensor 6 against an organism. The CPU 10 adjusts a pressurizing level of the sensor 6 against the organism by means of the bladder 9 via a pressure control circuit 71. The blood pressure monitor 7 functions as a blood detecting unit, and the sensor unit 13 functions as a pule wave measuring unit.

When the sensor 6 is pressurized against a wrist, it detects a pulse wave via a radial artery. The detected pulse wave signal is amplified by the sensor amplifier 5 into a predetermined level, and the amplified signal is converted into digital information by an A/D converter 51 so as to be given to the CPU 10.

The operation key 1D and the ten key 3 input information and instruction to the PC 1 by means of an external operation. The memory card 2 is attached to the PC 1, and information stored in the memory card 2 is accessed by CPU control in the PC 1.

FIG. 2 illustrates a state that the main body 1A of the PC 1 in FIG. 1 contains the printer 4, the sensor amplifier 5, the ten key 3 and the blood pressure monitor 7.

In this embodiment, the pulse wave monitoring device for supporting a diagnosis shown in FIGS. 1 to 3 calculates AI, which has calculating simplicity equivalent to the blood pressure measurement and is circulator information different from blood pressure information. AI and a blood pressure value are displayed in a related manner, and information which is used for doctor's understanding of a state of a patient's circulatory system to be diagnosed is displayed on the indicator 1B so as to support the diagnosis. The information is displayed on the indicator 1B in such a manner that the CPU 10 executes a predetermined program prestored in the memory 11. The CPU 10, therefore, has a display section 10B for displaying such information on the indicator 1B.

AI is a publicly-known index, and is mainly an index indicative of characteristic parameters of pulse wave reflection intensity corresponding to arteriosclerosis of central blood vessel (which is reflection phenomenon of a pulse wave and is easiness of accepting delivery blood flow). AI is particularly an index which is effective for early detection of cardiovascular disease, and it is known that AI represents a movement different from that of the blood pressure. AI is calculated from a monitored pulse wave. The sensor unit 13 is attached to a wrist by using an attachment belt or the like, the pressure control circuit 71 adjusts pressure and simultaneously the bladder 9 pressurizes the sensor 6 against the wrist so that the pulse wave is detected. AI is calculated based on the detected pulse wave in such a manner that the CPU 10 of the PC 1 executes a predetermined program prestored in the memory 11. The CPU 10, therefore, has a pulse wave characteristic parameter computation section 10A which serves as a pulse wave characteristic parameter computation unit.

Figure 4:
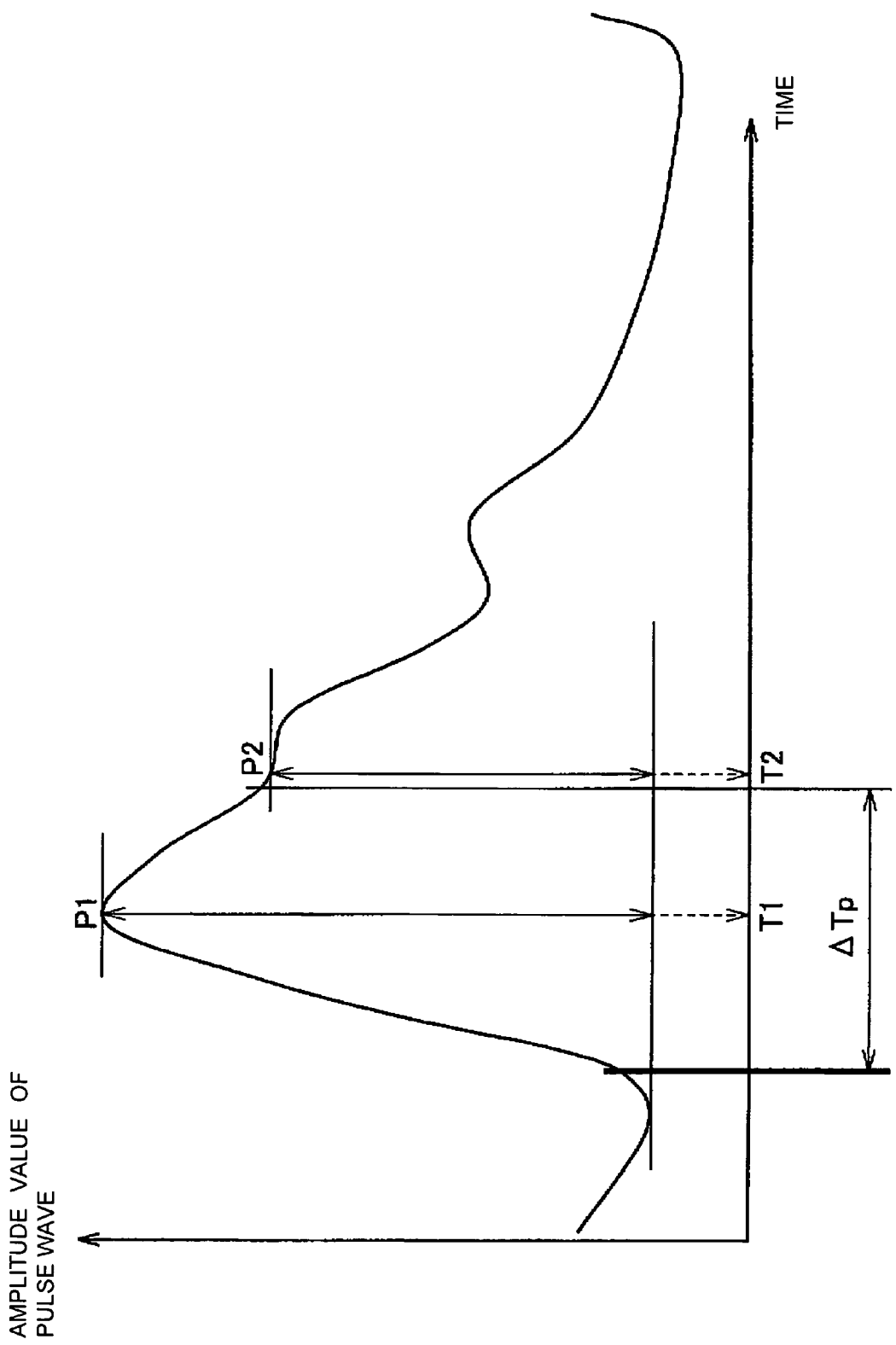
FIG. 4 is a diagram illustrating one example of a change in a pulse wave according to passage of time.
Figure 5:
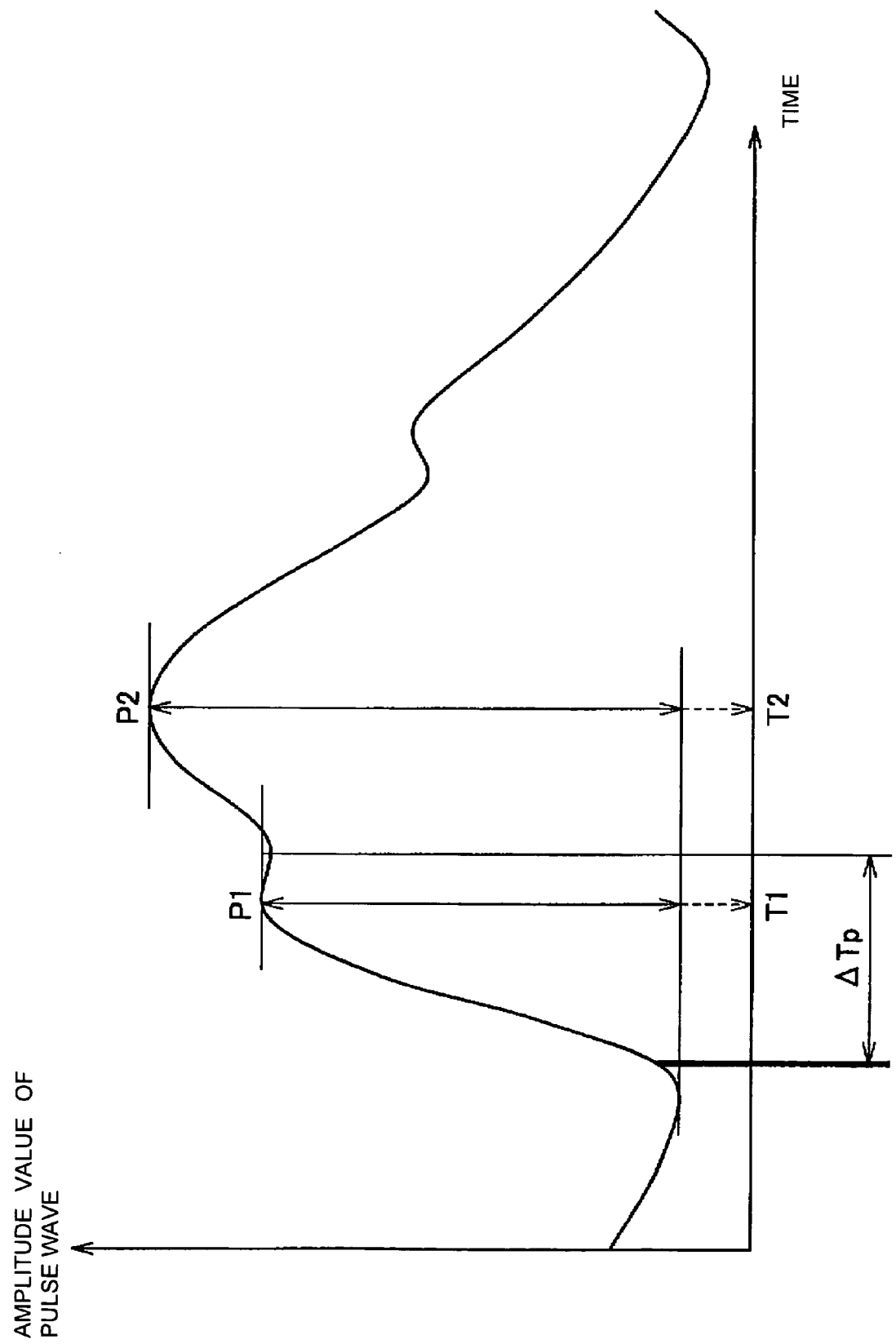
FIG. 5 is a diagram illustrating another example of the change in a pulse wave according to passage of time.

FIGS. 4 and 5 illustrates a change of the pulse wave to be detected according to passage of time. For example, when a pulse wave shown in FIG. 4 is detected, the computation can be performed in a manner that AI=P1/P2 (or AI (%)=(P1−P2)/P1*100). When a pulse wave shown in FIG. 5 is detected, the computation can be performed in a manner that AI=P1/P2 (or AI (%)=(P2−P1)/P2*100). A level P1 at time T1 represents a peak value obtained from a blood ejected wave of heart beat, and a level P2 at time T2 represents a peak value of the ejected wave of the hear beat obtained from a reflection wave. In the reflection wave, intensity and occurrence time phase change in response to blood vessel sclerosis. AI, therefore, represents a ratio of a peak value of a traveling wave component corresponding to the ejected wave included in the monitored pulse waveform to a peak value of a reflection wave component. A method of performing a computing operation such as differentiation or the like on the pulse waveform can be used as the method of determining the levels P1 and P2. In general, as to young people, a correlation such that level P2<level P1 is established as shown in FIG. 4. As to some old people, a correlation such that level P2>level P1 is established as shown in FIG. 5. This is because the ejected wave cannot be sufficiently absorbed by a vascular wall due to progress of sclerosis (arteriosclerosis) of the intravascular wall, and thus the reflection wave with high level is detected within short time.

ΔTp is related with a distance from a heart generating the ejected wave to a reflection wave generating portion and a pulse wave velocity (acceleration). When the level of the reflection wave generated in a portion close to the heart is high, therefore, ΔTp becomes small. It is known that when the intravascular wall is sclerosed, the pulse wave is quickly propagated. Further, it is known that when ΔTp is small, AI becomes large even if the level P2 of the reflection wave of the pulse wave does not change.

AI can be calculated in such a manner that a plurality (levels P1 and P2) of characteristic parameters (amplitude level of pulse wave (mV)) obtained directly from peaks as characteristic points of the pulse waveform are calculated and the characteristic parameters are computed.

Although this embodiment uses the above-mentioned AI, but the similar effect can be obtained by using ΔTp instead of AI. ΔTp is also a publicly-known index similarly to AI. ΔTp is described on pp 434-438 of the book "Hypertension" (September 2001, published by American Heart Association, Inc). ΔTp is occasionally represented also as TR (time reflection). TR is described on pp 263-270, 525.1 of "Journal of Physiology (2000)". ΔTp can be computed in such a manner that a plurality of characteristic parameters obtained directly from a position of a pulse wave rise point as the characteristic point of the pulse waveform and a starting position of the reflection wave (time (msec) corresponding to the position) are calculated and the characteristic parameters are calculated (differentiated).

Two direct causes of hypertension is known. One of them is an increase in a cardiac output (hereinafter, the factor 1), and the other is arteriosclerosis (hereinafter, the factor 2). These factors cannot be discriminated by blood pressure values, but AI changes according to a degree of the arteriosclerosis. When, therefore, both the blood pressure value and AI are checked, a determination can be made which of the two factors is the direct cause of hypertension.

When the cause is determined as the factor 1 (AI is small), a doctor can understand it is suitable to prescribe diuretic which reduces an amount of circulating fluid or beta-blocker which reduces an cardiac output. When the cause is determined as the factor 2 (AI is large), the doctor can understand it is suitable to prescribe Ca-antagonist, ACE inhibitor, AII receptor antagonist, alpha-blocker or the like which expands peripheral vessel as antihypertensive medicine. For this reason, information for supporting exact diagnosis and cure can be provided by displaying both the blood pressure value and AI.

Figure 6:
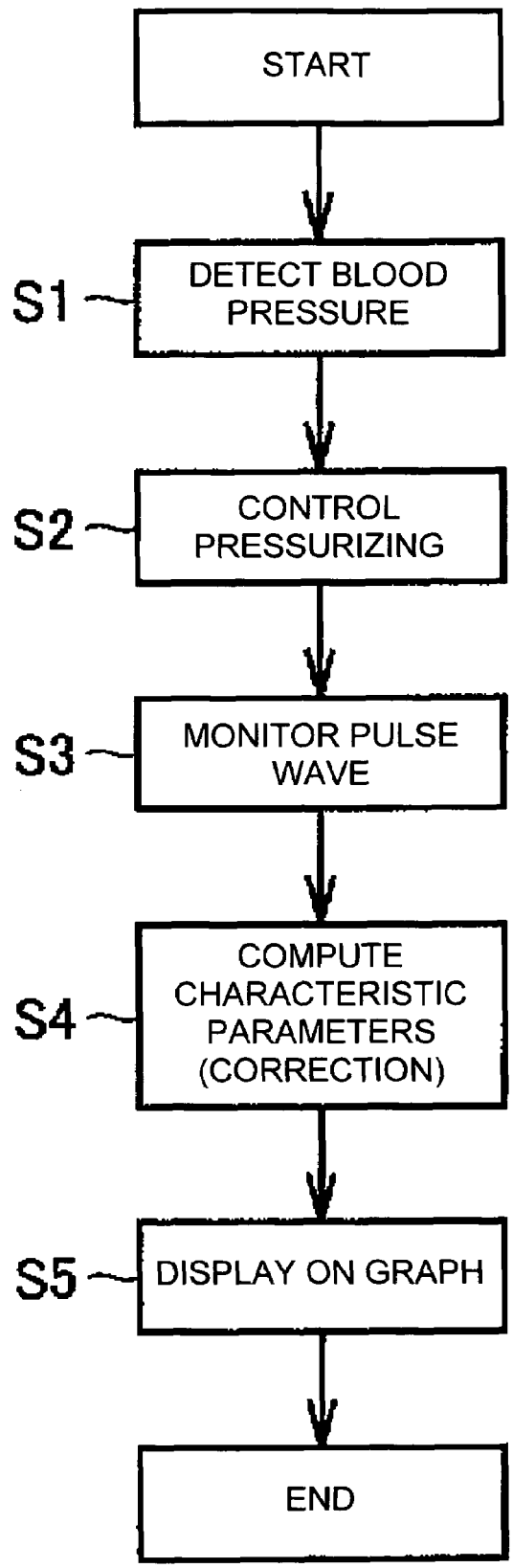
FIG. 6 is a processing flowchart illustrating one example of an operation from measurement to display of information.

An operation from the measurement to the provision of information is explained with reference to a processing procedure in FIG. 6. The procedure in FIG. 6 is executed in such a manner that the CPU 10 reads and executes a program prestored in the memory 11. The doctor operates the ten key 3 based on clinical recording information so as to input personal information such as patient ID, name, date of birth, sex, height and weight, and wound the arm band 8 around a portion on which the blood pressure is measured. The CPU 10 controls the pressure control circuit 71 to adjust the pressurizing level of the bladder of the arm band 8, and measures blood pressure based on a pulse wave detected by superposing the pressure wave. As a result, maximal blood pressure SYS and minimal blood pressure DIA, for example, are calculated by a publicly-known procedure (step S (hereinafter, S) 1). At this time, a pulse rate HR, mentioned later, may be calculated from the detected pulse wave by a publicly-known procedure.

The blood pressure monitor 7 monitors the information about blood pressure at real time, but information about blood pressure pre-measured and prepared (the maximal blood pressure SYS and the minimal blood pressure DIA) may be read from the memory card 2 or may be input through the ten key 3 (operation key 1D). It is assumed that the information about blood pressure is obtained by the measurement at real time.

While the CPU 10 is controlling the pressurizing level of radial artery obtained from the sensor 6 to an extent that the pulse waveform is not distorted, the CPU 10 measures (calculates) the pulse wave based on the output from the sensor 6 (S2 and S3). In the measurement of the pulse wave, a pressurized pulse wave of the radial artery measurable in a noninvasive manner is detected. Thereafter, the pulse wave characteristic parameter computation section 10A differentiates the pulse wave so as to obtain the above-mentioned levels P1 and P2 based on the measured pulse wave, and computes AI which is the characteristic parameter of the detected pulse wave (S4).

In the computation of the characteristic parameter, the pulse wave characteristic parameter computation section 10A executes an adjusting process according to information about each patient's body. When AI, $\Delta Tp$ and $\Delta Tpp$, mentioned later, are adjusted by using patient's age and sex as adjustment factors, more accurate information about the patient is occasionally provided. Further, when a pulse rate HR is high (the pulse is quick), AI becomes small, and thus the adjustment is made by using the pulse rate HR as the adjustment factor. In the case of $\Delta Tp$ and $\Delta Tpp$, adjustment using the pulse rate HR is not necessary. It is known that as a patient is taller, $\Delta Tp$ and $\Delta Tpp$ become larger. For this reason, $\Delta Tp$ and $\Delta Tpp$ are adjusted according to patient's height, but AI does not occasionally require a adjustment according to a height. The adjustment factors are not limited to them, and one of the adjustment factors may be used or a plurality of them may be combined to be used in the adjustment.

The adjustment factors for the correcting process can be specified by operating the ten key 3 or the operation key 1D, for example, so as to input the adjustment factors. The pulse wave characteristic parameter computation section 10A of the CPU 10 selects and apply a computing equation which is prepared for the adjustment based on a type of the input and specified adjustment factor. In order to adjust AI using the pulse rate HR as the adjustment factor, (Equation 1) is applied. Further, in order to adjust $\Delta Tp$ (or $\Delta Tpp$) using a height as the adjustment factor, (equation 2) in which a standard height Lstd and a patient's height Lp are used.

AI which is adjusted by the standard pulse rate=AI (measured value)+coefficient×(pulse rate HR−standard pulse rate) . . . (Equation 1).

$\Delta Tp$ (or $\Delta Tpp$) which is adjusted by the average height=$\Delta Tp$ (or $\Delta Tpp$)×(Lstds/Lp) . . . (Equation 2).

The display section 10B displays a graph in which the measured blood pressure is related with the adjusted AI on the indicator 1B (S5). As a result, a series of the process is ended.

Figure 7:
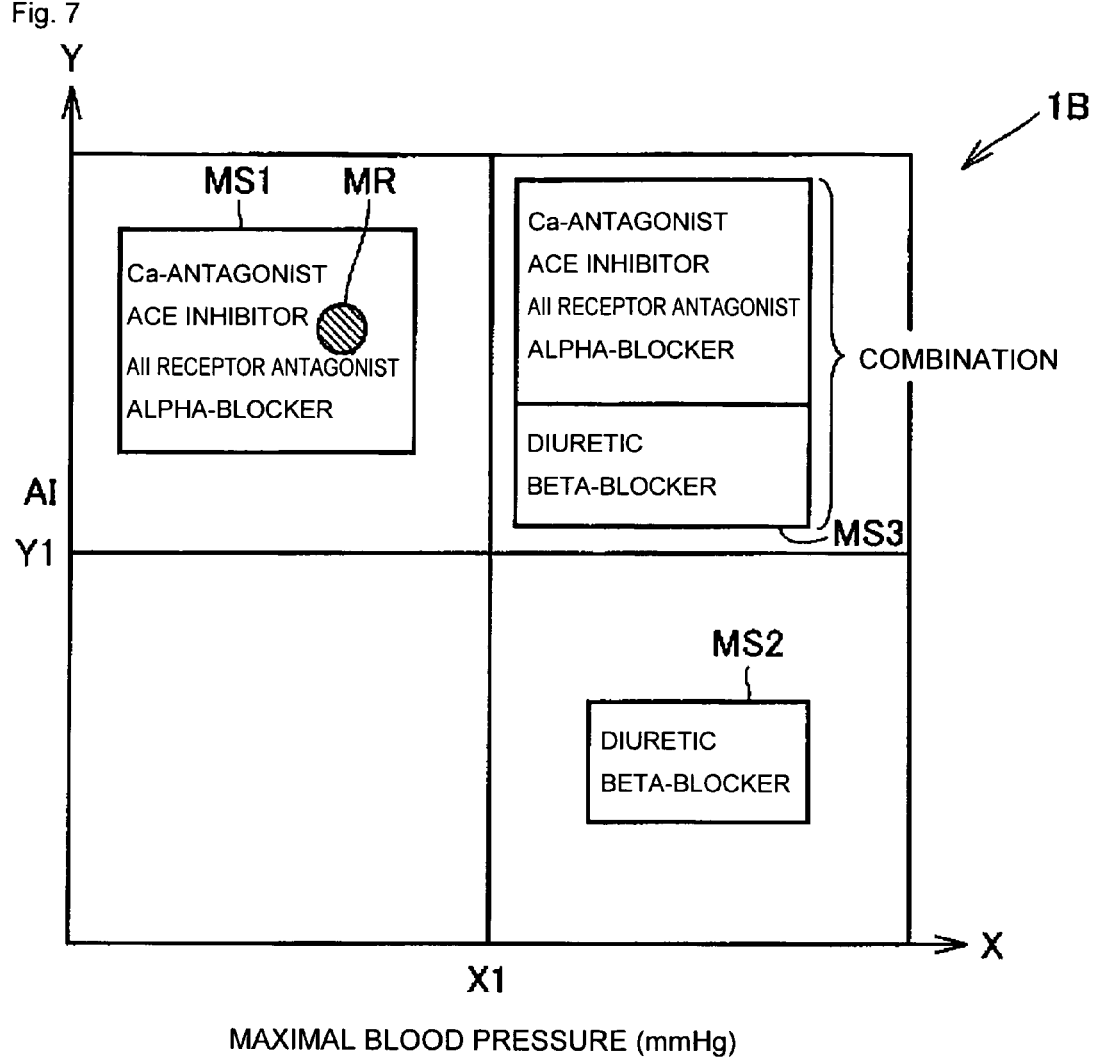
FIG. 7 is a diagram illustrating one example of display.

A concrete method of displaying the graph in which the blood pressure is related with AI is shown in FIG. 7, for example. A display example of FIG. 7 shows a two-dimensional graph in which the maximal blood pressure SYS (mmHg) is plotted along a horizontal axis X and AI is plotted along a vertical axis. In the graph, AI and the maximal blood pressure SYS are drawn in a related manner, threshold values X1 and Y1 of the blood pressure and AI are provided, and the graph is divided into four quadrants by the threshold values X1 and Y1. Further, the displaying section 10B displays names of medicine to be prescribed according to an AI level and a blood pressure value in the quadrants as messages MS1, MS2 and MS3 on the quadrants, respectively. For this reason, this can support a doctor's determination as to medicine to be prescribed.

The threshold values X1 and Y1 of the blood pressure and AI correspond to a predetermined level for diagnosing pathology. For example, when the maximal blood pressure SYS is lower than the threshold value X1 but AI is higher than the threshold value Y1, a diagnosis is made that peripheral vessel is sclerosed (in the progress of the arteriosclerosis), and information about medicine which softens a blood vessel shown in the message MS1 is displayed. When the maximal blood pressure SYS is higher than the threshold value X1 but AI is lower than the threshold value Y1, a diagnosis is made that a cardiac output is high, and information about medicine for reducing a blood amount is displayed in the message MS2. When the maximal blood pressure SYS and AI are higher than the threshold values X1 and Y1, a diagnosis is made that the peripheral vessel is sclerosal and the cardiac output is high, and information that medicine for softening the blood vessel displayed in the message MS3 and medicine for reducing a blood pressure amount should be prescribed. As a result, this method can support the diagnoses and the prescription of medicine.

It is assumed that the threshold values X1 and Y1 and the messages MS1 to MS3 in FIG. 7 are prestored in the memory 11. The messages MS1 to MS3 are prestored according to combinations of AI and the maximal blood pressure SYS. In the display of FIG. 7, the displaying section 10B reads one of the messages MS1 to MS3 from the memory 11 and displays the selected one message according to the quadrants (the level combinations of AI and the maximal blood pressure SYS).

In FIG. 7, a mark MR is shown in a two-dimensional coordinate (SYS, AI) represented by the measured AI and maximal blood pressure SYS. For this reason, it is easy for a doctor to determine a diagnosis and medicine to be prescribed for a patient (in other words, the factor of the hypertension is diagnosed) based on a display position of the mark MR.

Figure 8:
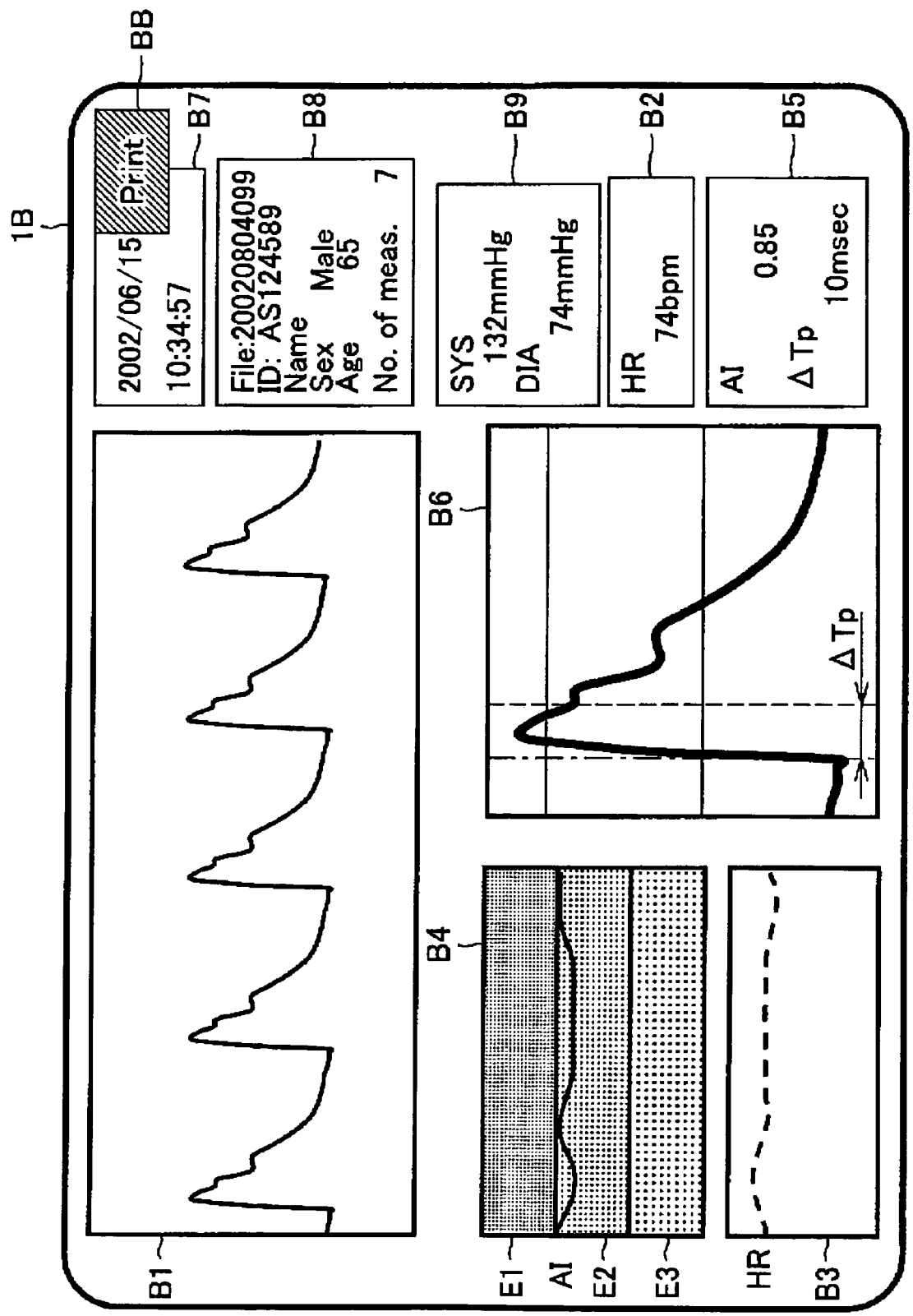
FIG. 8 is a diagram illustrating another example of the display.

Another display example of the measured AI and blood pressure is shown in FIG. 8. On a screen of FIG. 8, a detected pulse waveform is displayed on a portion B1, and an average pulse rate HR and a change with time in the pulse rate HR are displayed on portions B2 and B3, respectively. A change with time in AI is displayed on a portion B4, and average AI and ΔTp are displayed on a portion B5. A waveform according to FIG. 4 or 5 which is cut out per pulse is displayed on a portion B6, and a measurement date is displayed on a portion B7. Information for specifying a patient is displayed on a portion B8, and the maximal blood pressure SYS and the minimal blood pressure DIA are displayed on a portion B9. Also a button BB is displayed. When the button BB is clicked by operating the operation key 1D, displayed contents can be printed via the printer 4. The displayed information according to the change with time can be displayed in such a manner that the RTC 12 plots a value which is calculated in relation with the pulse wave detection time.

Areas E1, E2 and E3 are colored with different colors so that a relative level of AI is easily understood in the graph of the change with time in AI on the portion B4. The respective colors represent levels of the AI average values and SD (standard deviation) of patient's age and sex. Alternatively, the colors represent categories of AI values corresponding to, for example, 0.5, 0.75 and 0.9 indicating a survival rate of 5 years or 10 years obtained from clinical results of MEGA STUDY (Koukoushikessyo Shihango Kenkyukai).

The blood pressure and the change in AI according to the progress of cure are plotted on one graph in a chronological order, so that effects of administered medicine and cure can be displayed clearly. For this reason, a pulse wave data table TB shown in FIGS. 9A and 9B is stored in the memory 11 of the pulse wave monitoring device.

Figure 9A:
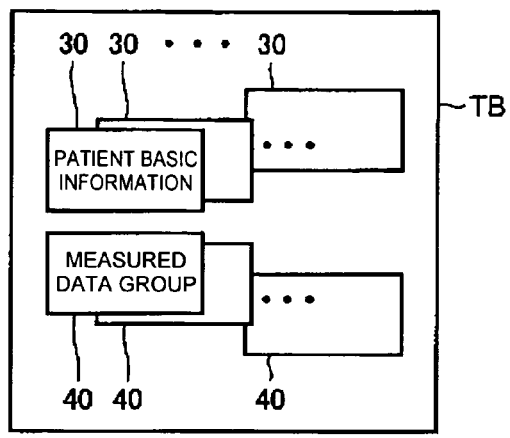
FIGS. 9A and 9B are diagrams illustrating pulse wave data tables.
Figure 9B:
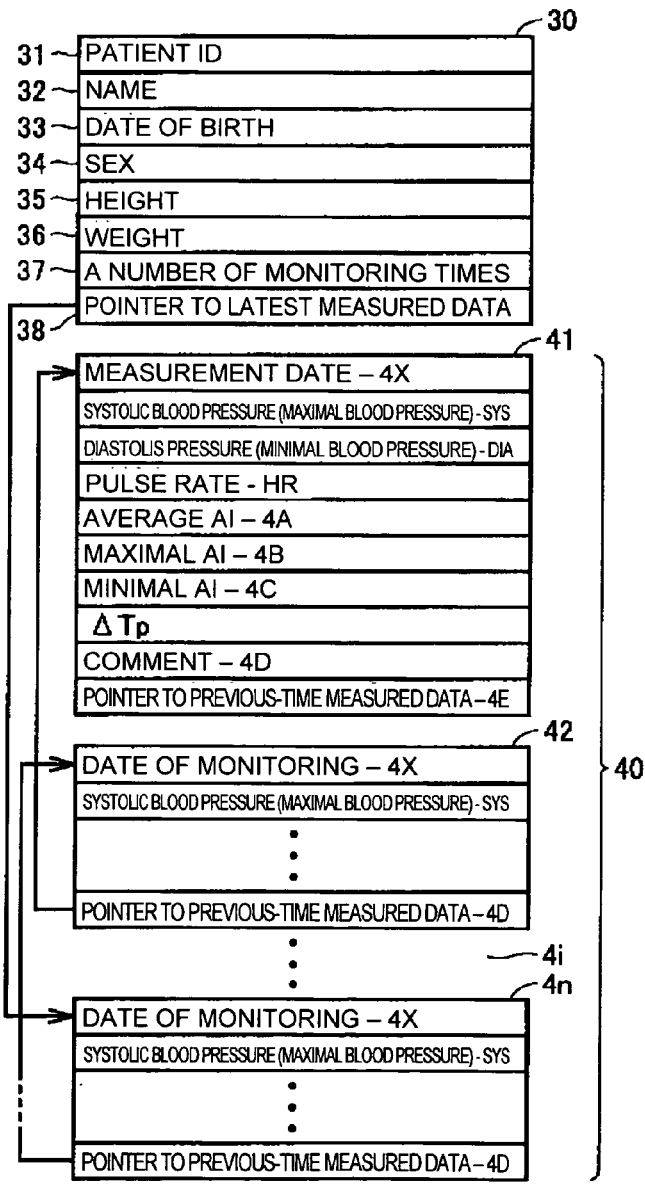

As shown in FIG. 9A, patient's basic information 30 and a measured data group 40 of each patient are stored in the pulse wave data table TB in a related manner. As shown in FIG. 9B, a patient ID 31, a name 32, a date of birth 33, a sex 34, a height 35, a weight 36, a number of measuring times 37 in the pulse wave monitoring device, and a pointer 38 led to the latest measured data for each patient. The measured data group 40 includes measured data 4i (i=1, 2, 3, ... , n) obtained every time of the measurement in the pulse wave monitoring device. The pointer 38 indicates the latest measured data 4i in the corresponding measured data 4i.

The measured data 4i includes a measurement date 4X, a maximal blood pressure SYS, a minimal blood pressure DIA, a pule rate HR, data 4A, 4B and 4C representing average AI, maximal AI and minimal AI, ΔTp, a doctor's comment 4D relating to prescribed medicine, and a pointer 4E led to the previous-time measured data 4i. In the case of the first measured data 41, the pointer 4E indicates "NULL", but the pointer 4E on and after the second measured data 4i indicates the previous-time measured data 4 (i−1). AI, ΔTp and HR are calculated and stored in the measured data group 40 in FIG. 9B according to the chronological order of the measurement date 4X, but similarly another kind of index such as ΔTpp, mentioned later, may be calculated to be stored.

A process for displaying the change in the blood pressure and AI on one graph in a chronological order is explained below according to a procedure of FIG. 10. It is assumed that the patient's basic information 30 and the measured data group 40 for a patient undergoing the measurement are prestored in the pulse wave data table TB.

The blood pressure measuring step (S1) to the characteristic parameter computing step (S4) are executed similarly to FIG. 6. At this time, a patient ID is input via the operation key 1D.

The CPU 10 accesses to the pulse wave data table TB in the memory 11 (S5). Concretely, the CPU 10 stores the measured data 4i obtained by this measurement into the measured data group 40, and carries out searching based on the input patient ID, so as to specify patient information 30 having the matched patient ID 31. The CPU 10 updates the pointer 38 of the specified patient information 30 so that the pointer 38 indicates the measured data 4i stored this time, and sets the pointer 4E of the stored and measured data 4i at this time so that the pointer 4E indicates the measured data 4 (i−1). When the measured data 4i at this time are stored in such a manner, the displaying section 10B executes a display process. Concretely, the displaying section 10B extracts (reads) the patient information 30 specified based on the patient, and extracts one or more kinds of indices and blood pressures (maximal blood pressure SYS) from plural pieces of the corresponding measured data 4i (data group). The display section 10B displays the extracted patient information 30 on the indicator 1B, and displays values of the extracted indices and the blood pressure which are indicated graphically in a chronological order on the indicator 1B according to the measurement date 4X (S6). A series of the process is ended here.

It is assumed that the patient information 30 and the measured data group 40 are prestored, but if not, the information about the patient input this time is newly stored as the patient information 30, and the measured data at this time are newly stored as the measured data 41 in the corresponding patient data group 40. Since only the measured data 41 for one patient are stored in the stored measured data group 40 in this case, therefore, the information can be displayed in the form shown in FIG. 7 or 8.

Figure 10:
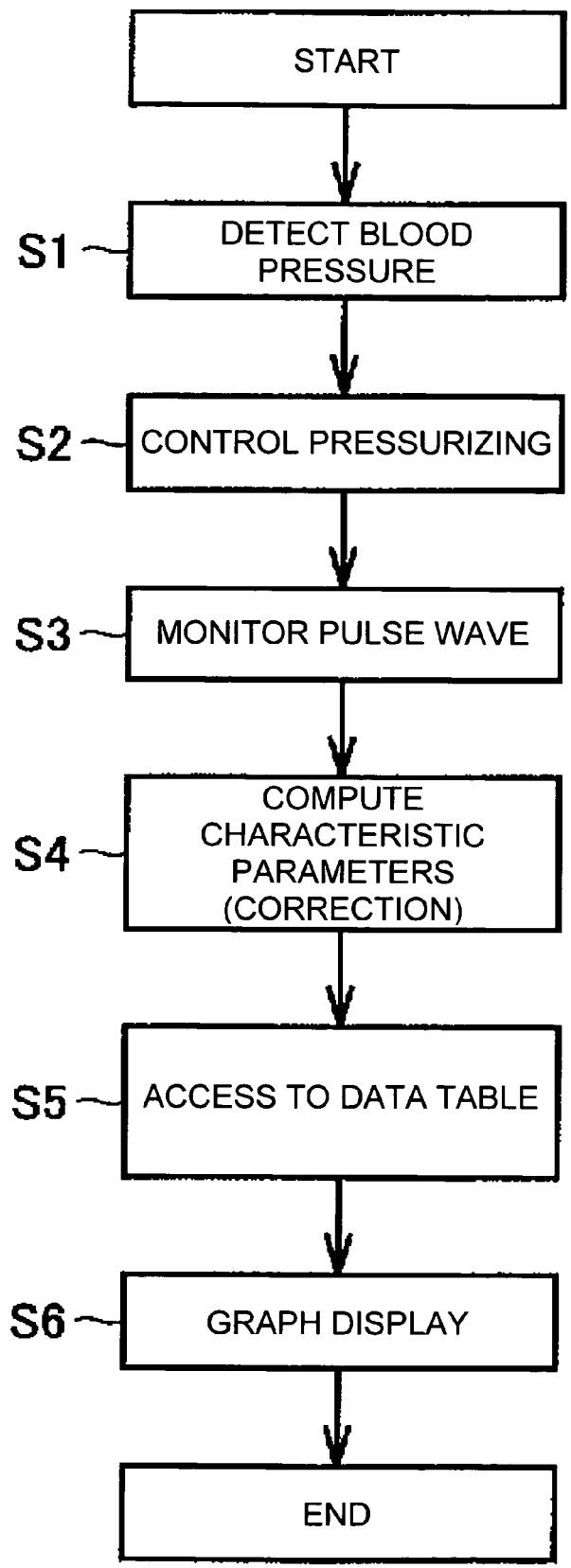
FIG. 10 is a processing flowchart illustrating another example of the operation from the measurement to the display of information.
Figure 11:
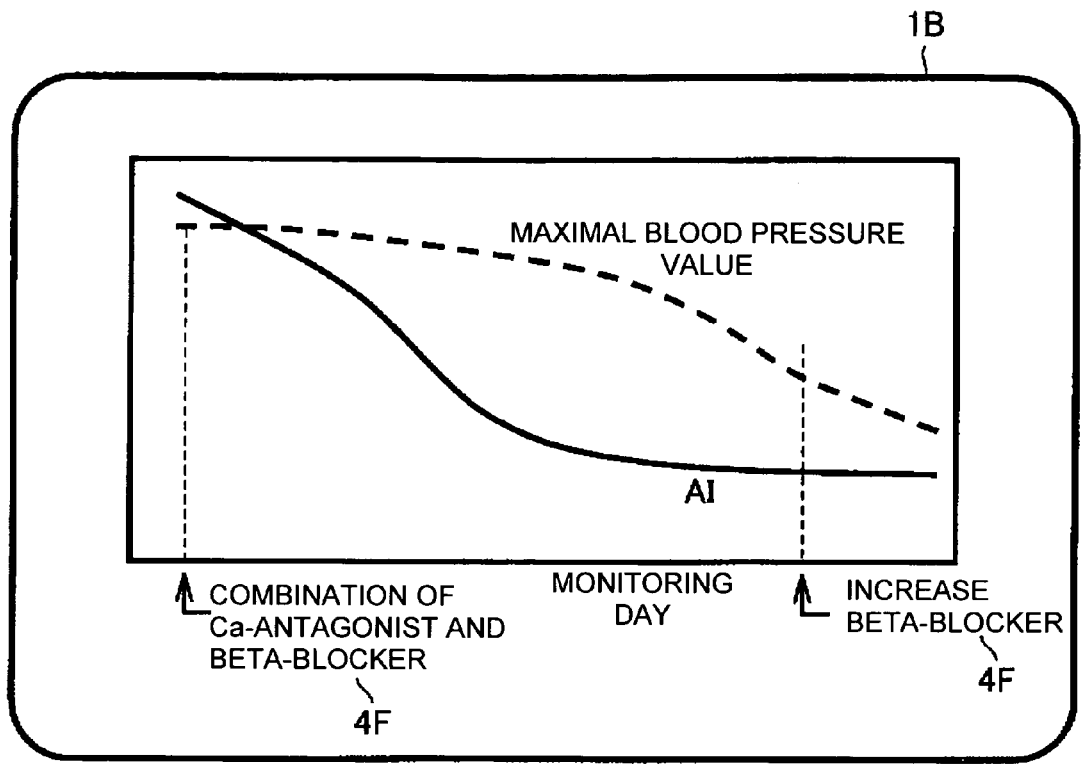
FIG. 11 is a diagram illustrating still another example of the display.

On example of the chronological order display (S6) in FIG. 10 is shown in FIG. 11. In FIG. 11, a measurement date is plotted along a horizontal axis, and the maximal blood pressure SYS and AI level are plotted along a vertical axis. The measured data 4i in the read measured data group 40 are arranged in a chronological order based on the pointer 4D, and the maximal blood pressure SYS and AI (for example, average AI) are read from the measured data 4i. The maximal blood pressure SYS and AI are plotted by a broken line and a solid line correspondingly to the measurement date so as to be displayed on the graph in FIG. 11 in a related manner.

In FIG. 11, also the information about the effects of the medicine prescribed for cure is displayed. That is to say, a comment 4F is displayed based on the commend 4D of the read measured data 4i according to a measurement date on the graph corresponding to the measurement date 4X. Since the comment 4F indicates prescribed medicine shown in the commend 4D, a doctor checks the graph, so as to be capable of getting information about temporal effect of administered medicine (a change in the maximal blood pressure SYS and a change in AI)

Figure 12:
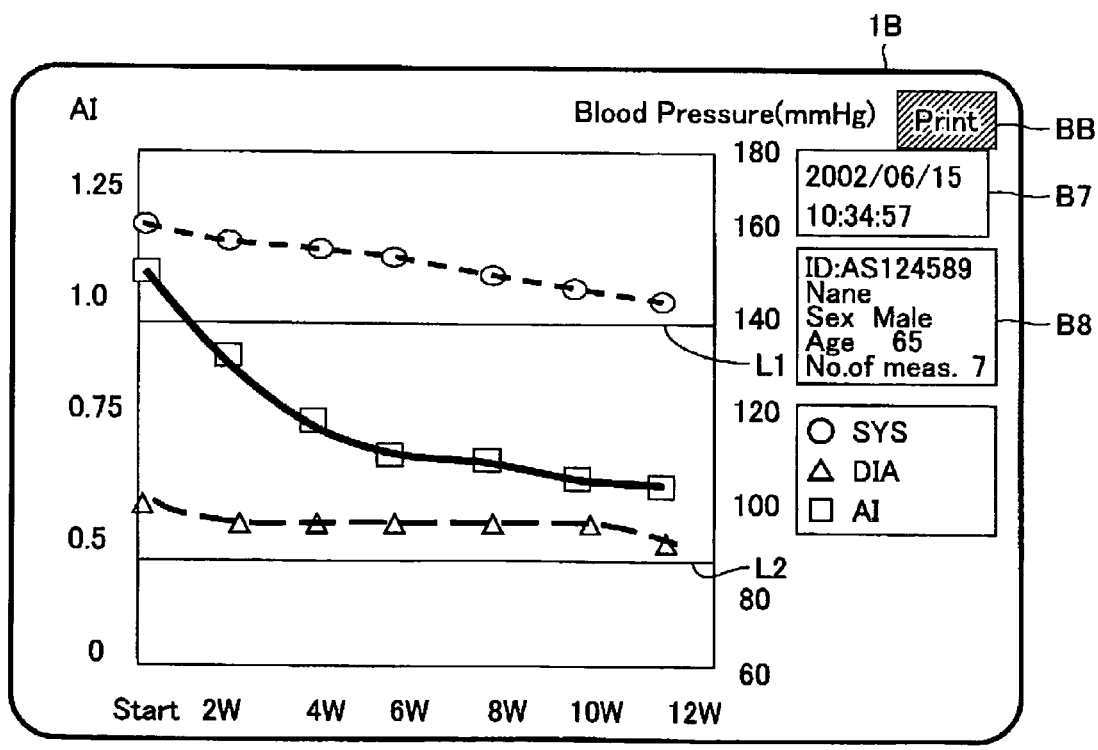
FIG. 12 is a diagram illustrating still another example of the display.

Another example of the chronological order display is shown in FIG. 12. On a graph of FIG. 12, time (weekly unit) is plotted along a horizontal axis, and the AI level and blood pressure (mmHg) are plotted along a vertical axis. Changes in the maximal blood pressure SYS, the minimal blood pressure DIA and AI according to passage of time are plotted graphically. Information about the button BB and the portion B7 and B8 are shown on a screen of FIG. 12. The doctor checks the graph of FIG. 12 with passage of antihypertensive cure in clinical recording, so as to easily understand the effect of the cure. Lines L1 and L2 shown on the graph of FIG. 12 correspond to, for example, a hypertension threshold value 140/90 mmHg of 1999 WHO/ISH.

Figure 13:
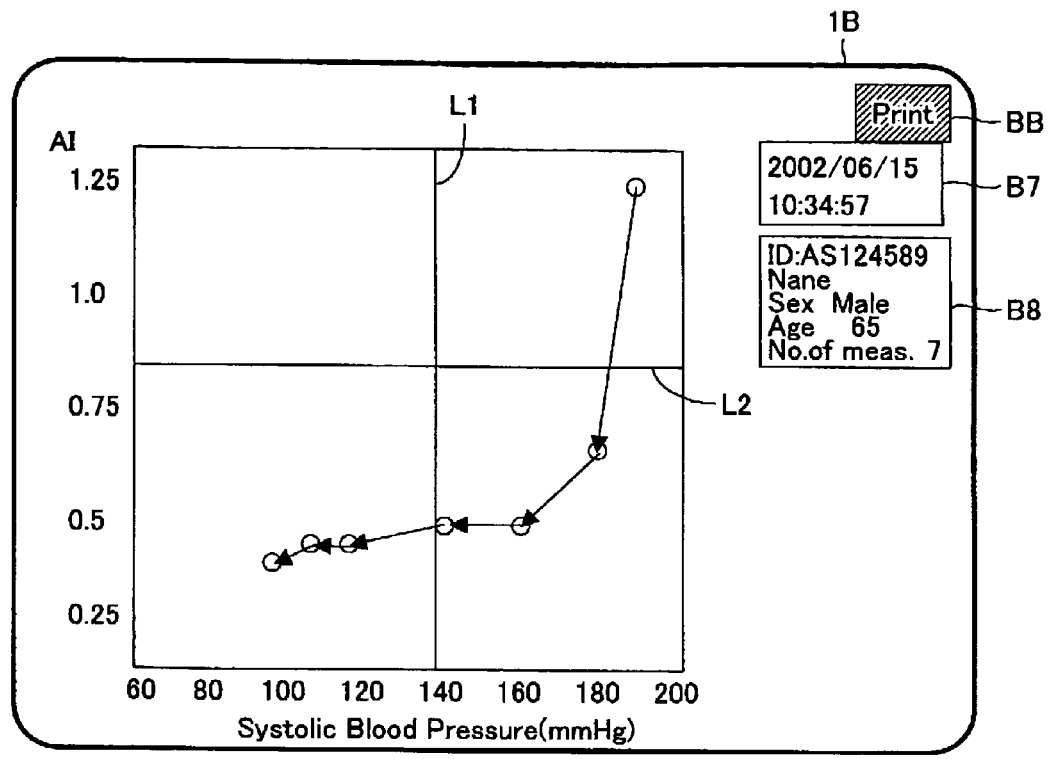
FIG. 13 is a diagram illustrating still another example of the display.

Still another example of the chronological order display is shown in FIG. 13. On the graph of FIG. 13, the maximal blood pressure SYS (mmHg) is plotted along a horizontal axis, and the AI level is plotted along a vertical axis. A change in a correlation between the maximal blood pressure SYS and AI according to the passage of time of the measurement date 4X is plotted graphically. Also the information about the button BB and the portions B7 and B8 shown in FIG. 8 is displayed on the screen of FIG. 13.

In FIG. 13, the maximal blood pressures SYS and AI measured at a plurality of times are indicated on a two-dimensional graph, and the correlation therebetween is shown. At the first measurement, the doctor checks this graph so as to understand a condition of the patient in a more detailed manner than the information about only blood pressure. An example of the measured data and a diagnostic example of the doctor are as follows.

That is to say, when the maximal blood pressure SYS is not high and AI is low, the condition of the patient is determined as being normal, and when the maximal blood pressure SYS is not high and AI is high, a determination is made that hypertension and arteriosclerosis progress in the future. When the maximal blood pressure SYS is high and AI is low, a determination is made that cure for reducing a cardiac output and an amount of body fluid is necessary. When the maximal blood pressure SYS is high and AI is high, a determination is made that immediate cure is necessary.

The graph of FIG. 13 is checked with the passage of the antihypertensive cure in the clinical recording, so that the effect of the cure can be easily understood. The line L1 shown vertically with respect to the axis of the blood pressure on the graph of FIG. 13 shows, for example, systolic blood pressure value of 140 mmHg of the hypertension of 1999 WHO/ISH. The line L2 shown vertically with respect to the axis of AI shows AI which is sorted into a predetermined survival rate such as 5-year survival rate or 10-year survival rate obtained from the clinical results of MEGA STUDY.

Figure 14:
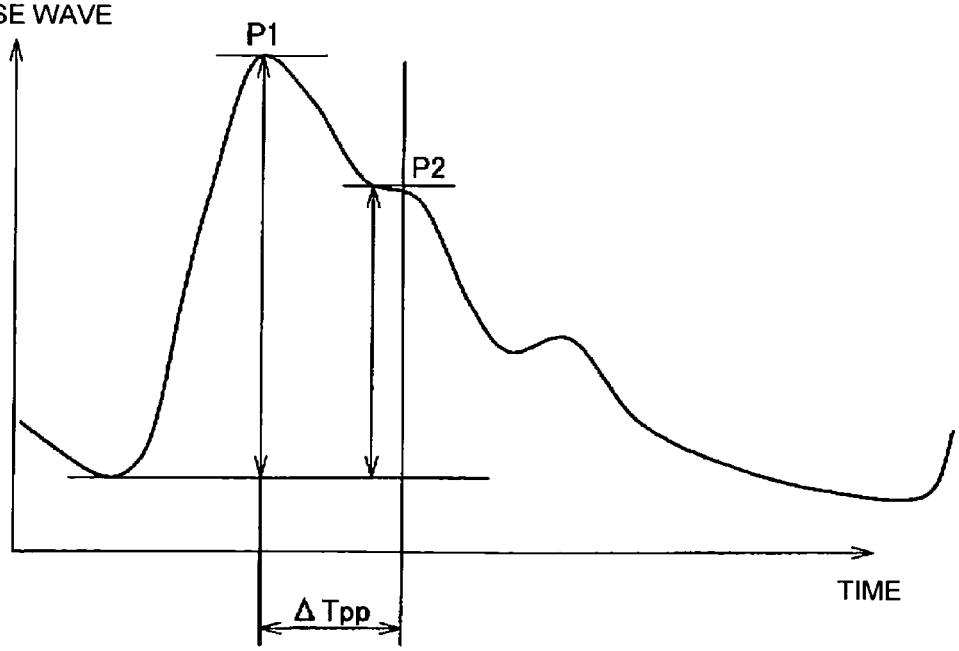
FIG. 14 is a diagram illustrating $\Delta Tpp$ based on a pulse wave.

As explained with reference FIG. 4 or 5, a rise point of the pulsating wave is recognized in order to obtain ΔTp, but when the rise is unclear, it is difficult to calculate ΔTp accurately. In this case, therefore, ΔTpp may be used as an index to be replaced by ΔTp. ΔTpp is an index representing a time difference between peaks of the pulsating wave and a reflection wave as shown in FIG. 14. The time difference between the peaks of both waves is clear and is easily recognized. ΔTTp can be calculated by computation (difference) of the characteristic parameters obtained by calculating characteristic parameters (time (msec) corresponding to the peaks) obtained directly from the peak positions of the pulsating wave and the reflection wave as characteristic points of the pulse wave.

Figure 15:
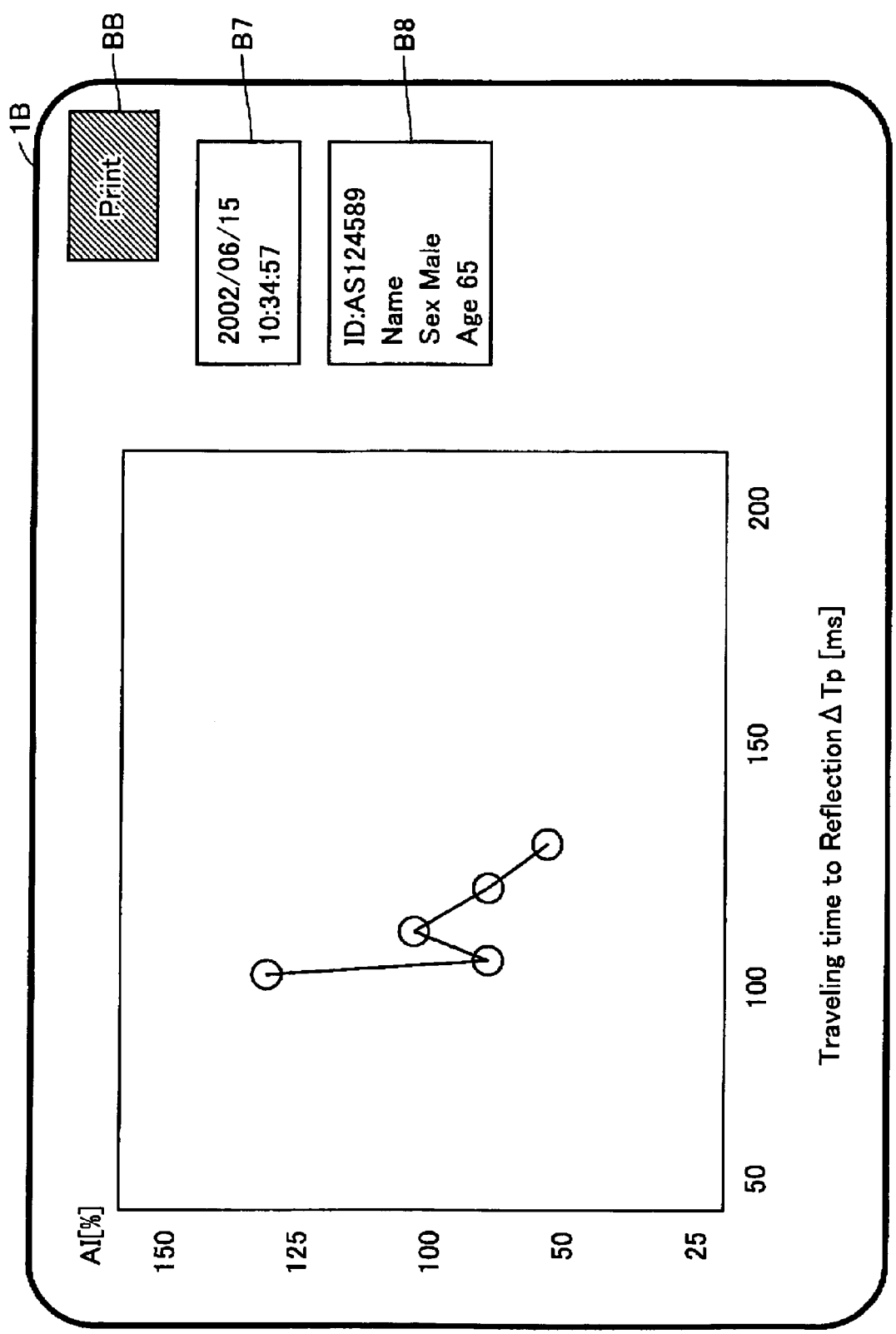
FIG. 15 is a diagram illustrating one example of the display in which AI is related with $\Delta Tp$.

In addition to the display form in which the maximal blood pressure SYS and AI are related based on the measurement date 4X in FIGS. 7 and 11, AI and ΔTp in chronological order stored in the measured data group 40 may be related to be displayed as shown in FIG. 15. When only AI is displayed, as shown in FIG. 4 or 5, only information about intensity (level P2) of the reflection wave from the pulse wave and the pulse wave velocity (occurrence time phase of the reflection wave from the ejected wave) is displayed as a synthesized index. As shown in FIG. 14, therefore, AI is plotted along an X axis and ΔTp is plotted along a Y axis. AI and ΔTp are plotted on a two-dimensional plane according to chronological order, so that scattering of the reflection wave intensity (a degree of convergence (overlap condition)) represented by AI in the time phase shown by ΔTp can be displayed. When low AI is converged on a phase in which ΔTp is comparatively small, therefore, the reflection wave with high level is detected in a concentrated manner for comparatively short time. For this reason, a state that the ejected wave cannot be sufficiently absorbed by a vascular wall, namely, a diagnosis is made that sclerosis of the vascular wall (arteriosclerosis) progresses.

A set of the information displayed in a related manner on the two-dimensional plane may be composed of AI and ΔTpp, or AI and the pulse rate HR stored in the chronological order of the measured data group 40.

Other Display Forms

Figure 16:
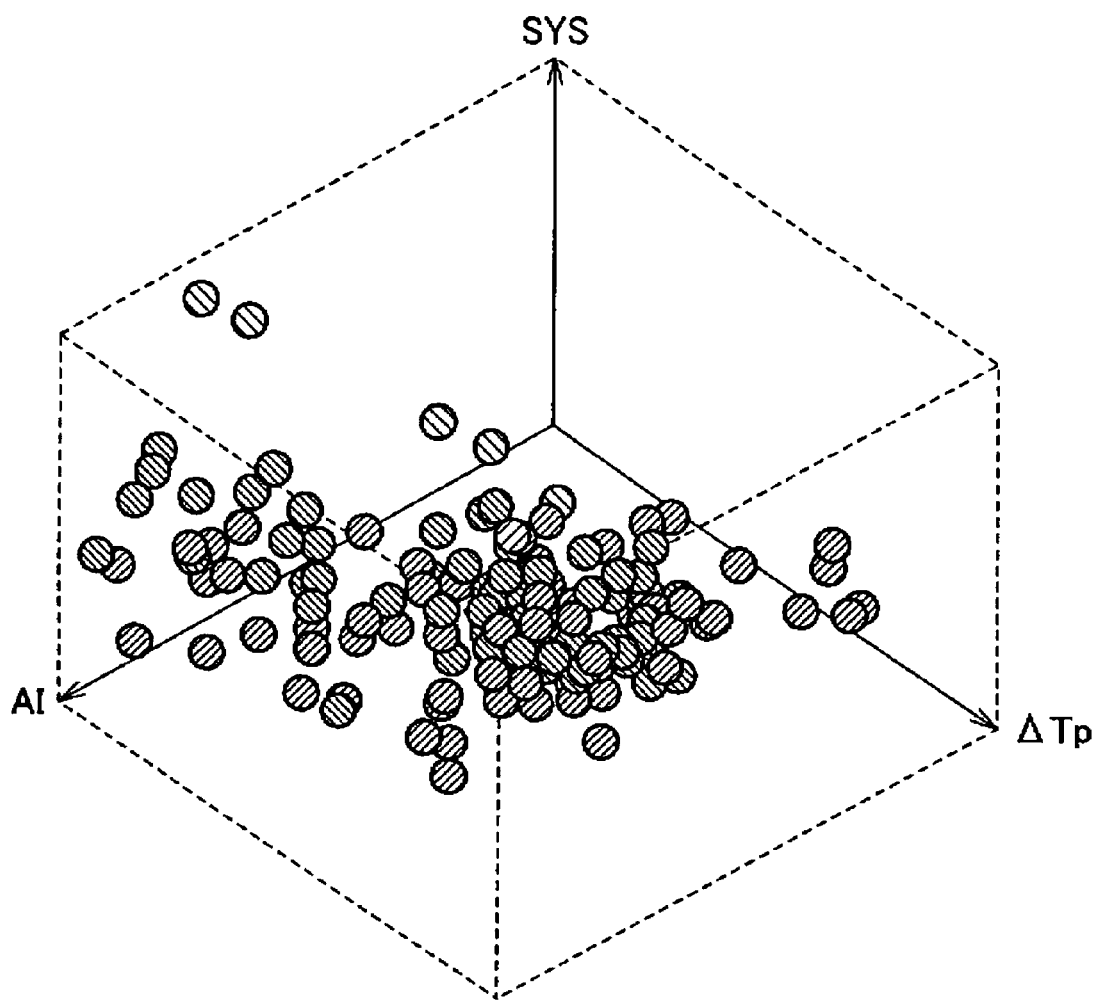
FIG. 16 is a diagram illustrating one example of display in which AI, $\Delta Tp$ and a maximal blood pressure SYS are related with each other.

The display section 10B may relate two kinds of indices and the maximal blood pressure SYS stored in the measured data group 40 obtained from the characteristic parameters of the pulse waveform with each other according to the chronological order of the measurement date 4X, so as to display them on the indicator 1B. In FIG. 16, AI is plotted along an X axis, ΔTp is plotted along a Y axis, and the maximal blood pressure SYS is plotted along a Z axis. Three pieces of information can be related to be displayed on a three-dimensional space composed of X, Y and Z.

When an attention is paid to points which are plotted on positions in the three-dimensional space as shown in FIG. 16, this can support the diagnosis of a load to a heart explained in FIG. 7 based on the relating between the maximal blood pressure SYS and AI on the X-Z plane. When the information about the relating between AI and ΔTp on the X-Y plane corresponding to the points is taken into consideration, this can support the diagnosis of the causes of the load as explained in FIG. 14.

Further, when the maximal blood pressure SYS, and AI and ΔTp (or ΔTpp) as indices are related to be displayed, the mode shown in FIG. 17 may be displayed. In FIG. 17, AI is plotted along a horizontal axis, and the maximal blood pressure SYS and ΔTp are plotted along two vertical axes. In this case, the relating between AI and the maximal blood pressure SYS on one plane according to the measurement date 4X, and the relating between AI and ΔTp according to the measurement date 4X can be displayed simultaneously. For this reason, the mode shown in FIG. 17 can support the diagnosis explained in FIG. 16.

The three pieces of information displayed simultaneously in the related manner may be composed of the pulse rate HR, AI and ΔTp (or ΔTpp), or may be composed of the maximal blood pressure SYS, the pulse rate HR and AI. Types of the information to be combined are not limited.

A number of pieces of the information which is related to be displayed simultaneously is not limited to two or three, and may be four or more.

In addition, in FIGS. 13, 15, 16 and 17, the information about medicine to be prescribed may be displayed as shown in FIG. 7 according to a level of the related indices or according to a level of the related indices and blood pressure.

The related indices and information are displayed on the indicator 1B as shown in FIGS. 7, 8, 11, 12, 13, 15, 16 and 17. They may be, however, output to an output device such as a printer, not shown, by graphic printing, or may be transferred to another system.

The embodiments disclosed this time are considered in all respects as illustrative and not restrictive. The scope of the present invention is indicated by the appended claims rather than by the foregoing description and all changes which come within the meaning and range of equivalency of the claims are therefore intended to be embraced therein.

What is claimed is:

1. A pulse wave monitoring device comprising:
   a pulse wave detection device configured to detect a pulse wave of a subject;
   a computation unit that identifies a plurality of characteristic points of the pulse wave detected by the pulse wave detection device, calculates a plurality of characteristic parameters corresponding to the identified characteristic points and calculates an index indicative of a pulse wave reflection by performing a computation on the characteristic parameters;
   a blood pressure measuring device configured to measure a blood pressure of the subject; and
   a display unit that shows, on a two-dimensional graph, the calculated index on a first axis and the measured blood pressure on a second axis and wherein the display unit further shows a prescription with a mark, wherein the position of the mark on the graph represents a correlation between the calculated index and the measured blood pressure of the subject.

2. The pulse wave monitoring device of claim 1, wherein a first characteristic point of the characteristic points corresponds to a peak of a traveling wave component of the detected pulse wave and a second characteristic point of the characteristic points correspond to a peak of a reflection wave component of the detected pulse wave, the reflection wave component being generated as a result of a reflection of the traveling wave component, and the index is a ratio of amplitudes of the pulse wave at the first and second characteristic points.

3. The pulse wave monitoring device of claim 1, wherein a first characteristic point of the characteristic points corresponds to a traveling wave component of the detected pulse wave and a second characteristic point of the characteristic points correspond to a reflection wave component of the detected pulse wave, the reflection wave component being generated as a result of a reflection of the traveling wave component, and the index is a time difference between the first and second characteristic points.

4. The pulse wave monitoring device of claim 2, wherein the index comprises an augmentation index.

5. The pulse wave monitoring device of claim 4, wherein the computation unit adjusts the calculated augmentation index based on a pulse of the subject.

6. The pulse wave monitoring device of claim 3, wherein the index comprises ΔTp.

7. The pulse wave monitoring device of claim 6, wherein the computation unit adjusts the calculated ΔTp based on a height of the subject.

8. A pulse wave monitoring device comprising:
   a pulse wave detection device configured to detect a pulse wave of a subject;
   a computation unit that calculates a plurality of different indices based on a wave form of the detected pulse wave, each of the different indices being indicative of a pulse wave reflection; and
   a display unit that shows, on a two-dimensional graph, a correlation between at least two of the different indices and wherein the display unit further shows a prescription with a mark, where the position of the mark on the graph represents the correlation between the at least two of the different indices.

9. The pulse wave monitoring device of claim 8, further comprising a blood pressure measuring device configured to measure a blood pressure of the subject, wherein the display unit is configured to show a correlation between the measured blood pressure and at least one of the different indices.

10. The pulse wave monitoring device of claim 9, further comprising a memory device that stores a plurality of the calculated indices for each of the different indices and a plurality of the measured blood pressures in a chronological order.

11. The pulse wave monitoring device of claim 10, wherein the display unit shows the calculated indices stored in the memory device for at least one of the different indices and the measured blood pressures stored in the memory device in the chronological order.

12. The pulse wave monitoring device of claim 1, wherein the display unit shows a plurality of possible prescriptions, each corresponding to a range of correlations between calculated indices and measured blood pressures, wherein the prescription with the mark is a selected one of the plurality of possible prescriptions for which the mark falls within a corresponding range.

* * * * *